United States Patent [19]

Zakoshansky et al.

[11] Patent Number: 5,502,259
[45] Date of Patent: Mar. 26, 1996

[54] METHOD FOR PURIFICATION OF PHENOL

[75] Inventors: Vladimir M. Zakoshansky; Irina I. Vasilieva; Andrei K. Griaznov, all of St. Petersburg, Russian Federation

[73] Assignees: General Electric Company, U.S.A.; Illa International, U.S.S.R.

[21] Appl. No.: 290,258

[22] Filed: Aug. 15, 1994

[30] Foreign Application Priority Data

Dec. 1, 1993 [RU] Russian Federation ....... 93-053966/04

[51] Int. Cl.$^6$ ............................ C07C 37/68; C07C 37/70
[52] U.S. Cl. ..................... 568/754; 568/749; 568/768; 568/798
[58] Field of Search ............................ 568/741, 754, 568/768, 798, 749

[56] References Cited

U.S. PATENT DOCUMENTS

| | | | |
|---|---|---|---|
| 2,948,758 | 8/1960 | Filar | 568/754 |
| 3,029,294 | 4/1962 | Keeble | 568/754 |
| 3,454,653 | 7/1969 | Larson | 568/754 |
| 4,504,364 | 3/1985 | Chen et al. | 568/754 |

OTHER PUBLICATIONS

Concise Encyclopedia of Chemical Technology Kirt–Othmer–A Wiley–Interscience Publication–John Wiley & Sons.

*Primary Examiner*—Werren B. Lone

[57] ABSTRACT

The invention relates to a method for purification of phenol and specifically to a method for purification of phenol produced within the process of joint phenol and acetone production by cumene method.

The aim of the invention is to develop a catalyst which has high activity for phenol purification from organic micoimpurities with regeneration of the catalyst and which has high mechanical strength and stability with long catalyst life.

This result is obtained by phenol purification using a heterogeneous zeolite catalyst. The acidity of the catalyst measured by butane cracking ($K_A$) is more than 10.

It is preferable to use zeolites which are designated according to the classification of the International Zeolite Association by indices FAU (zeolites X, Y), MFI (for example, ZSM-5), MOR (mordenite), MAZ (omega), BEA (beta), FER (ferrierite) and others. These zeolites can be used with binders (aluminum oxide, silica gel, aluminosilicates or aluminophosphates) and without them. It is preferable to use zeolite of the Y type with an aluminosilicate binder and a the value of $K_A=50$–$80$ cm$^3$/min*g and Si/Al ratio more than 3. The concentration of sodium, potassium and other alkali agents on the basis of their oxides does not exceed 2 wt %, preferably not more than 0.3 wt %. It is preferable to use zeolites with medium and large pores. Size of zeolites pores should be within the range 4 Å in diameter and more. The most preferable zeolites are with large pores (>6 Å in diameter) such as Y and mordenite.

19 Claims, No Drawings

METHOD FOR PURIFICATION OF PHENOL

BACKGROUND OF THE INVENTION

The present invention relates to a method of purification of phenol and in particular, to a method of purification of phenol which is produced within joint phenol and acetone production by the cumene method.

Phenol, after being distilled from heavy and light products of the joint synthesis, still contains the impurities of organic matters such as mesityl oxide, alpha-methylstyrene, 2-methylbenzofurane and other carbonyl compounds which are difficult to remove by conventional methods such as, for example, distillation. These impurities worsen the properties of commercial phenol since such phenol has low color stability.

A widely known commercial method of phenol purification from organic micro-impurities is a method based on phenol contact with ion-exchange resins as taught in Technology report: "Development of process scheme for phenol purification at ion-exchange KY-2, KY-2-8γc for Ufa Plant of Synthetic Alcohol", Giprokauchuk, Novokuibyshevsk, 1986, p. 84. The disadvantages of this method are a narrow temperature range of resin application (50°– 130° C.), limited life of usage due to unrecoverable destruction of catalyst granules as well as problems of spent resin utilization.

U.S. Pat. No. 3,454,653 and U.S. Pat. No. 3,029,294 describe methods of phenol purification from impurities using aluminosilica catalysts. Disadvantages of these methods are low catalyst activity and, hence, long contact time (4–8 hours), as well as selective purification from one of the impurities components (in U.S. Pat. No. 3,454,653 from 2-methylbenzofurane, in U.S. Pat. No. 3,029,294 from hydroxyacetone).

The purpose of the present invention is the development of a catalyst with high activity for phenol purification from impurities with efficient regeneration, high mechanical strength and stability to give a long catalyst life.

This purpose is achieved by phenol purification using heterogeneous zeolite catalysts which are distinguished by the certain level of acidity, measured, for example, by a method of butane cracking as described in H. Rastlli, Can. Journal of Chem. Eng., 1982, v. 60, p. 44–49). All zeolites with $K_A>10$, where $K_A$—first order reaction rate constant for butane cm$^3$/min*g can be used as catalysts for catalytic phenol purification in the liquid phase.

It is preferable to use zeolites which are designated according to classification of International Zeolite Association by indices FAU (zeolites X,Y,), MFI (for example, ZSM-5), MOR (mordenite), MAZ (omega), BEA (beta), FER (ferrierite) and others. These zeolites can be used with binders (aluminum oxide, silica gel, aluminosilicates or aluminophosphates) and without them. It is preferable to use zeolite of Y type with an aluminosilicate binder having a value of $K_A=50–80$ cm$^3$/min*g and Si/Al ratio more than 3. Preferably, the concentration of sodium, potassium and other alkali agents on the basis of their oxides does not exceed 2 wt %, more preferably not more than 0.3 wt %. It is preferable to use zeolites with medium and large pores. Size of zeolites pores should range from 4 Å in diameter and higher. The most preferable zeolites are with large pores (>6 Å) such as Y and mordenite.

Phenol derived from distillation of heavies and lights and still containing the impurities hydroxyacetone, mesityl oxide, alpha-methylstyrene, 2-methylbenzofurane and other carbonyl compounds but not containing water (water content less than 1 wt %, preferably less than 0.1 wt %) contacts the zeolite catalyst at a temperature of between about 120° to 250° C. (preferably 180°–200° C.) and space velocities 0.1–3.5 hr$^{-1}$ (preferably 0.8–1.2 hr$^{-1}$).

It has been discovered that said purification results in not less than 90% conversion of such impurities as mesityl oxide, hydroxyacetone, alpha-methylstyrene and other carbonyl compounds. It is important that the above mentioned impurities are converted into the products of condensation under the effect of the catalyst and purification conditions, so that these impurities can be separated from phenol by further rectification and removed from the process along with other "heavy" products, so-called "phenol tar". At high space velocities, (more than 0.8 hr$^{-1}$) there is a rise in the level of 2-methylbenzofurane to an amount which can be easily removed from phenol by distillation. At low space velocities (less than 0.8 hr$^{-1}$) and high temperatures (more than 200° C.) there is a decrease in 2-methylbenzofurane amount (conversion is not more than 50%). Acidity of zeolites active centers can be stabilized by rare-earth elements (e.g. lanthanum and others). This results in a stable catalyst run over an extended time even at high micro-impurities content in the phenol to be purified. The useful life of the above mentioned catalysts is not less than three years.

The present invention is illustrated by the following examples which do not limit the invention and its claims but illustrate the application of a number of zeolite catalysts of the type suitable for phenol purification:

EXAMPLE 1

Phenol containing 21 ppm acetone, 66 ppm hydroxyacetone (HA), 217 ppm mesityl oxide (MO), 1304 ppm alpha-methylstyrene (AMS), 236 ppm 2-methylbenzofurane (2-MBF) and 35 ppm of other carbonyl compounds (CC) was pumped through a reactor pipe with a length of 1500 mm., an inner diameter of 30 mm, filled with 950 ml of catalyst (Zeolite of Y-type with an aluminosilicate binder. Zeolite content 16%, aluminum oxide content 9.7%, silicon oxide content 86.1%, sodium oxide content—0.3% rare-earth elements oxides content—2.9%, specific pore volume—0.51 cm$^3$/g, and an acidity level determined by the value of $K_A=70$ cm$^3$/min*g) at a temperature of 140° C., atmospheric pressure, a space velocity of 0.3 hr$^{-1}$. After the catalyst run, phenol purity was determined by gas chromatography (GC). Samples for analysis were grabbed each hour. Time of the experiment was 5 hours. Phenol composition after purification was as follows (average values): 5 ppm MO (the degree of conversion 98% ), 25 ppm AMS (the degree of conversion 98%), 4 ppm CC, 10 ppm acetone, 1 ppm HA and 269 ppm 2-MBF (increase —) (13%).

EXAMPLE 2

The experiment was conducted as described in Example 1 but the space velocity was 3.5 (hr$^{-1}$). The phenol composition before purification was as follows: 5 ppm acetone, 96 ppm HA, 53 ppm OM, 1106 ppm AMS and 214 ppm 2-MBF; phenol composition after purification was as follows: 4 ppm OM (the degree of conversion was 92% ), 21 ppm AMS (the degree of conversion was 98% ), 6 ppm CC, 12 ppm acetone, there is no hydroxyacetone, 237 ppm 2-MBF (increase— 11%).

EXAMPLE 3

The experiment was conducted as described in Example 1 but temperature was 250° C., space velocity 0.1 hr$^{-1}$. The phenol composition before purification was as follows: 21 ppm acetone, 107 ppm OM, 98 ppm HA, 230 ppm AMS and 152 ppm 2-MBF: the phenol composition after purification was as follows: 8 ppm OM (the degree of conversion 93% ), 3 ppm AMS (the degree of conversion 99% ) and 45 ppm 2-MBF (the degree of conversion 70%), CC—9 ppm, acetone—10 ppm, no hydroxyacetone.

EXAMPLE 4

The experiment was conducted the same way as described in Example 3 but space velocity was 3.5 ($hr^{-1}$). The phenol composition before purification was as follows: 23 ppm acetone, 63 ppm OM, 5 ppm AMS and 178 ppm 2-MBF; the phenol composition after purification was as follows: 6 ppm OM (the degree of conversion 90%), 2 ppm AMS (the degree of conversion 96%) and 201 ppm 2-MBF (increase—13%), CC—5 ppm, 8 ppm acetone, hydroxyacetone was not found.

EXAMPLE 5

The present example illustrates the effect of water in crude phenol on the catalyst and the resulting change in conversion of mesityl oxide, alpha-methylstyrene and 2-methylbenzofurane.

The experiment was conducted the same way as described in Example 1. The catalyst was first calcinated in a nitrogen stream at a temperature of 250° C. The loss in weight at calcination was 2 wt %. The results of the experiment are given below (see Table 1).

velocity varied from 0.4 to 3.75 ($hr^{-1}$). Atmospheric pressure was used or those pressures which matched the state of liquid phenol. The obtained results are shown in table 2.

TABLE 1

| Water concentration in crude phenol, wt % | Conversion (%) | | | | The degree of 2-MBF increase, % | |
|---|---|---|---|---|---|---|
| | mesityl oxide | | &-methylstyrene | | | |
| | calcined catalyst | noncalcined catalyst | calcined catalyst | noncalcined catalyst | calcined catalyst | noncalcined catalyst |
| 0.1 | 93 | 91 | 99 | 99 | 15 | 20 |
| 0.4 | 90 | 87 | 99 | 99 | 20 | 19 |
| 0.8 | 89 | 85 | 98 | 98 | 51 | 44 |
| 1.2 | 87 | 81 | 98 | 98 | 60 | 70 |
| 1.6 | 81 | 77 | 98 | 98 | 61 | 59 |
| 2.0 | 75 | 71 | 97 | 96 | 83 | 81 |
| 2.4 | 68 | 65 | 96 | 96 | 95 | 91 |

EXAMPLE 6

The present example illustrates the duration of catalyst run without loss of activity.

The experiment was conducted the same way as described in Example 1. The unit was operated continuously for 1043 hours. Temperature varied from 115° to 190° C., space

TABLE 2

| Total run time, hr | Number of measurements | Mean space velocity $hr^{-1}$ | Average temperature. °C. | Position | Average imp. composition ppm | | |
|---|---|---|---|---|---|---|---|
| | | | | | OM | AMS | 2MBF |
| 92 | 9 | 0.7 (0.4–1.0) | 123 (116–128) | input output residue, % | 24 — 0 | 421 4 1 | 145 187 129 |
| 201 | 6 | 2.8 (2.2–3.75) | 142 (138–144) | input output residue, % | 86 6 7 | 125 4 3 | 198 433 219 |
| 278 | 4 | 2.2 (2.0–2.4) | 132 (131–132) | input output residue, % | 80 7 9 | 391 10 3 | 188 256 136 |
| 492 | 7 | 1.0 (1.3–0.6) | 141 (132–149) | input output residue, % | 50 4 8 | 883 11 1 | 183 308 168 |
| 682 | 9 | 0.95 (1.3–0.6) | 150 (141–156) | input output | 42 2 | 229 10 | 207 443 |

TABLE 2-continued

| Total run time, hr | Number of measurements | Mean space velocity hr$^{-1}$ | Average temperature. °C. | Position | Average imp. composition ppm | | |
|---|---|---|---|---|---|---|---|
| | | | | | OM | AMS | 2MBF |
| 1043 | 12 | 1.6 (1.2–2.6) | 187 (185–190) | residue, % | 2 | 4 | 214 |
| | | | | input | 38 | 81 | 125 |
| | | | | output | 2 | 3 | 311 |
| | | | | residue, % | 5 | 4 | 249 |

Note: In the columns "mean space velocity" and "average temperature", the minimum and maximum values of corresponding variables, are given in brackets.

EXAMPLE 7

The experiment was conducted the same way as described in Example 1–4 but catalyst with following characteristics was used: Zeolite of Y type with binder aluminosilicate. Zeolite content was 7%, silicon oxide content 85%, aluminum oxide content 8.9%, sodium oxide content 0.3%, rare-earth elements oxides content 1.5%, the volume of pores—0.5 cm$^3$/g. The value of $K_A$=50 cm$^3$/min*g. The results are presented in table 3.

TABLE 3

| Conditions of experiment | Degree of conversion, % | | | | Increase, % |
|---|---|---|---|---|---|
| | OM | AMS | HA | CC | 2-MBF |
| Example 1 | 95 | 98 | 100 | 93 | 16 |
| Example 2 | 90 | 99 | 100 | 95 | 5 |
| Example 3 | 91 | 98 | 100 | 98 | –9 |
| Example 4 | 92 | 98 | 100 | 97 | 13 |

EXAMPLE 8

The experiment was conducted the same way as in Example 1, but zeolites X,Y and mordenite, MFI and FERRIERITE in H-form were used. The acidity of applied zeolites set by KA value is within range 30–90 cm$^3$/min*g. Zeolite-mordenite had no additions of aluminum and manganese. Results are given in table 4.

TABLE 4

| Conditions of experiment | $K_A$ cm$^3$/ min*g | Degree of conversion, % | | | | Increase, % |
|---|---|---|---|---|---|---|
| | | OM | AMS | HA | CC | 2-MBF |
| Mordenite | 80–90 | 100 | 99 | 100 | 93 | 1 |
| HY | 50–70 | 95 | 90 | 54 | 89 | 0 |
| HX | 30–50 | 80 | 65 | 45 | 98 | –10 |
| MFI | 80–90 | 98 | 90 | 91 | 87 | –15 |
| FERRIERITE | 40–50 | 82 | 67 | 50 | 95 | –18 |

EXAMPLE 9

The experiment was conducted the same way as described in Examples 6–8, but zeolites with binders were used. Aluminosilicates were used as binders (silicon oxide content is 70 wt %, aluminum oxide content is 30 wt %). Zeolites content is 10 wt %. Results are represented in table 5.

TABLE 5

| Conditions of experiment | $K_A$ cm$^3$/ min*g | Degree of conversion, % | | | | Increase, % |
|---|---|---|---|---|---|---|
| | | OM | AMS | HA | CC | 2-MBF |
| Mordenite | 75 | 100 | 99 | 98 | 93 | 5 |
| HY | 55 | 96 | 85 | 54 | 89 | 3 |
| HX | 35 | 78 | 61 | 45 | 98 | –3 |
| MFI | 70 | 96 | 95 | 91 | 87 | –5 |
| FERRIERITE | 40 | 82 | 67 | 50 | 95 | –20 |

EXAMPLE 10

Comparative, Overcome the Upper Limit of Space Velocity

The experiment was conducted the same way as described in Examples 2 and 4 but space velocity was 8 hr$^{-1}$. The phenol composition before purification was the following: 3 ppm acetone, 30 ppm OM, 1396 ppm AMS and 82 ppm 2-MBF. After purification phenol contained the following:

a) temperature 140° C.
  16 ppm OM   (the degree of conversion was 47%)
  17 ppm AMS  (the degree of conversion was 99%)
  60 ppm 2-MBF (the degree of conversion was 27%)
b) 13 ppm OM  (the degree of conversion was 53%)
  21 ppm AMS  (the degree of conversion was 98%)
  49 ppm 2-MBF (the degree of conversion was 40%)

EXAMPLE 11

Comparative, Catalyst Contains 50% Silicon Oxide, 42% Aluminum Oxide, and 2 % Sodium Oxide. Content of the Rest of the Components Matches the Catalyst in Example 1

Conditions of the example 1, 2, 3, 4. Phenol composition—96 ppm OM, 80 ppm AMS, 241 ppm 2-MBF, 100 ppm HA, 53 ppm CP. The results of purification are shown in table 6.

TABLE 6

| Conditions of experiment | Degree of conversion, % | | | | Increase, % |
|---|---|---|---|---|---|
| | OM | AMS | HA | CC | 2-MBF |
| Example 1 | 43 | 96 | 90 | 90 | 96 |
| Example 2 | 39 | 97 | 85 | 89 | 87 |
| Example 3 | 44 | 98 | 80 | 89 | 101 |
| Example 4 | 36 | 96 | 85 | 87 | 85 |

EXAMPLE 12

Comparative, Overcome the Upper Temperature Limit

The experiment was conducted the same way as described in Examples 1 and 2 but temperature was 300° C. Phenol composition before purification was the following: 21 ppm acetone, 46 ppm OM, ppm AMS and 218 ppm 2-MBF. The following was found in phenol after purification:

| a) space velocity | |
|---|---|
| −0.3 (hr$^{-1}$) | |
| 3 ppm OM | (the degree of conversion was 94%) |
| 4 ppm AMS | (the degree of conversion was 97%) |
| 391 ppm 2-MBF | (increase 57%) |
| b) space velocity | |
| −3.5 (hr$^{-1}$) | |
| 4 ppm OM | (the degree of conversion was 91%) |
| 5 ppm AMS | (the degree of conversion was 96%) |
| 391 ppm 2-MBF | (increase 79%) |

The example shows that there are no significant advantages in conducting the process at high temperatures, but energy requirements increase. GC analysis showed the presence of products of high condensation in amount≈2000 ppm. At 140°–200° C. the said products were not formed. This will probably lead to slight phenol losses.

What is claimed is:

1. A method for purification of phenol from carbonyl compounds and unsaturated compounds to increase activity, to increase catalyst life and to permit regeneration, comprising contacting the phenol with a zeolite catalyst with pores of more than 4 Å in diameter under atmospheric pressure or a pressure which matches the pressure of the liquid phenol and at a temperature of between about 120° to 250° C.

2. The method of claim 1 wherein the acidity of the zeolite catalyst measured in reaction of butane cracking is more than 10 ($K_A$ cm$^3$/g* min>10).

3. The method of claim 1 wherein the zeolite catalyst is selected from the group consisting of types of zeolite X, Y, mordenite, BETA, MFI, FERRIERITE.

4. The method of claim 2 wherein $Al_2O_3$, $SiO_2$, aluminosilicates or aluminophosphates are used as a binder.

5. The method of claim 1 wherein the content of Na, K and other alkaline agents in the catalyst on the basis of their oxides does not exceed 2 wt %.

6. The method of claim 1 wherein rare-earth elements are present in an amount of from 0 to 5 wt %.

7. The method of claim 1 wherein the zeolite concentration in the catalyst is from 5 to 100 wt %.

8. The method of claim 1 wherein the size of catalyst pores is more than 6 Å in diameter.

9. The method of claim 1 wherein the degree of purification from unsaturated compounds is not less than 90%.

10. The method of claim 1 wherein the degree of purification from mesityl oxide is not less than 90%.

11. The method of claim 1 wherein the degree of purification from hydroxyacetone is not less than 90%.

12. The method of claim 1 wherein purification from 2-methylbenzofurane at space velocities of more than 0.8 hr$^{-1}$ increases the 2-methylbenzofurane amount to a level which can be easily removed from phenol by distillation, and at space velocities of less than 0.8 hr$^{-1}$ and temperatures of more than 200° C. decreases the 2-methylbenzofurane amount to not more than 50%.

13. The method of claim 1 wherein the process is conducted at a temperature of from 180° to 200° C.

14. The method of claim 1 wherein the process is conducted at space velocities of 0.1–3.5 hr$^{-1}$.

15. The method of claim 1 wherein the process is conducted at a water content in phenol not more than 1 wt %.

16. The method of claim 1 wherein the catalyst life is not less than 3 years.

17. The method of claim 1 wherein the catalyst is contacted at a pressure of from 1 to 10 atmospheres in which the phenol and impurities contained in it are in the liquid phase.

18. The method of claim 1 wherein after phenol purification by contact with the catalyst and further rectification the phenol product is characterized by the following values:

SAD (test for carbonyl content in phenol)—not less than 96;

color by Pt—Co scale—5; and identified impurities including MO, AMS, HA, 2-MBF, acetone—not more than 100 ppm, including MO content not more than 2 ppm.

19. The method of claim 1 wherein the catalyst is not subjected to any preliminary thermal treatment, but provides phenol purification from impurities as effectively as calcined catalyst.

* * * * *